United States Patent
Han et al.

(10) Patent No.: US 9,580,738 B2
(45) Date of Patent: *Feb. 28, 2017

(54) **METHOD FOR PRODUCING EXTRACELLULAR PROTEINS FROM GENUS *TEPIDIMONAS***

(71) Applicant: INDUSTRIAL TECHNOLOGY RESEARCH INSTITUTE, Hsinchu (TW)

(72) Inventors: Yin-Lung Han, Tainan (TW); Jo-Shu Chang, Taichung (TW); Yung-Chong Lou, Tainan (TW); Chieh-Lun Cheng, Taoyuan (TW); Chih-Hsi Liu, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/838,612

(22) Filed: Aug. 28, 2015

(65) Prior Publication Data

US 2016/0186226 A1    Jun. 30, 2016

(30) Foreign Application Priority Data

Dec. 25, 2014 (TW) .............................. 103145419 A (51) Int. Cl.
*C12P 21/00* (2006.01)
(52) U.S. Cl.
CPC .................................... *C12P 21/00* (2013.01)
(58) Field of Classification Search
CPC ........................................................ C12P 21/00
See application file for complete search history.

(56) References Cited

U.S. PATENT DOCUMENTS

| | | | | |
|---|---|---|---|---|
| 8,129,155 | B2 * | 3/2012 | Trawick | ............... C12N 9/0006 435/146 |
| 8,728,777 | B2 | 5/2014 | Biton et al. | |
| 2004/0175407 | A1 | 9/2004 | McDaniel | |
| 2012/0058533 | A1 | 3/2012 | Biton et al. | |

FOREIGN PATENT DOCUMENTS

| CN | 102628025 A | 8/2012 |
|---|---|---|
| TW | 201328597 A | 7/2013 |
| TW | 201348442 A | 12/2013 |

OTHER PUBLICATIONS

Franca et al. International J of Systematic and Evolutionary Microbiology, 2006, 56:907-912.*
"Microorganisms; 133. Carbon Monoxide Oxidizer Medium," DSMZ GmbH, 2009, 1 page.
"Microorganisms; 27. Rhodospirillaceae Medium (modified)," DSMZ GmbH, 2007, 1 page.
Taiwanese Office Action and Search Report, dated Jan. 12, 2016, for Taiwanese Application No. 103145419.
Wan-Ju Yu et al., "Optimal environmental condition and medium composition for protein production of T. fonticaldi AT-A2," Conference on Biotechnology and Bioengineering of BEST, Jun. 28, 2013, 4 pages.
Albuquerque et al., "*Tepidimonas thermarum* sp. nov., a new slightly thermophilic betaproteobacterium isolated from the Elisenquelle in Aachen and emended description of the genus *Tepidimonas*", Systematic and Applied Microbiology 29, 2006, pp. 450-456.
Chen et al., "*Tepidimonas fonticaldi* sp. nov., a slightly thermophilic betaproteobacterium isolated from a hot spring", International Journal of Systematic and Evolutionary Microbiology, 2013, 63, pp. 1810-1816.
Chen et al., "*Tepidimonas taiwanensis* sp. nov., a novel alkaline-protease-producing bacterium isolated from a hot spring", Extremophiles, 2006, pp. 35-40.
Moreira et al., "*Tepidimonas ignava* gen. nov., sp. nov., a new chemolithoheterotrophic and slightly thermophilic member of the β-Proteobacteria" International Journal of Systematic and Evolutionary Microbiology, 2000, 50, pp. 735-742.

* cited by examiner

*Primary Examiner* — Bin Shen
(74) *Attorney, Agent, or Firm* — Birch, Stewart, Kolasch & Birch, LLP (57) ABSTRACT

The disclosure provides a method for producing extracellular proteins from genus *Tepidimonas*, including: performing a fermentation culturing to a bacteria of genus *Tepidimonas* with a culturing medium to form a fermented liquid, wherein the composition of the culturing medium includes a carbon source which is an organic acid, selected from a group consisting of acetate, lactate and butyrate; a nitrogen source selected from a group consisting of $(NH_4)_2SO_4$, $NH_4NO_3$, $NH_4Cl$ and urea; phosphate; carbonate; $MgCl_2$; yeast extract; and trace elements, and wherein the gas feeding rate for the fermentation culturing is about 0-0.1 vvm; and after the fermentation culturing is completed, collecting the fermented liquid, wherein the fermented liquid contains extracellular protein secreted from the bacteria of genus *Tepidimonas*.

38 Claims, 6 Drawing Sheets

METHOD FOR PRODUCING EXTRACELLULAR PROTEINS FROM GENUS *TEPIDIMONAS*

CROSS REFERENCE TO RELATED APPLICATION

The present application is based on, and claims priority from, Taiwan Application Serial Number 103145419, filed on Dec. 25, 2014, the disclosure of which is hereby incorporated by reference herein in its entirety.

TECHNICAL FIELD

The technical field relates to a method for producing extracellular proteins from genus *Tepidimonas*.

BACKGROUND

The inventors of the present disclosure have sampled the water samples of An-tong hot spring in Hualien County, Taiwan. Then, a novel bacterium of *Tepidimonas* named *Tepidimonas fonticaldi* sp. nov. in the water samples was isolated and purified. Extracellular proteins secreted by *Tepidimonas fonticaldi* sp. nov. have excellent effects for binding metal ions, and are not influenced by environmental conditions, such as high temperature, high pressure, or pH value. Therefore, the extracellular proteins secreted by *Tepidimonas fonticaldi* sp. nov. can prevent metal salt scaling, especially calcium carbonate, from being formed in boiler equipment, underground pipelines, geothermal wells, industrial wastewater or hard water, to maintain the proper functioning of the machines and reduce operating time and costs.

Bacteria of genus *Tepidimonas* are bacteria which are gram-negative, strictly aerobic, oxidase- and catalase-positive, rod-shaped and slightly thermophilic bacteria.

However, the growth and self-protein metabolizing rate of bacteria of genus *Tepidimonas* are slow, and this makes it hard to obtain the protein. Therefore, a novel method of producing extracellular proteins from genus *Tepidimonas* is needed.

SUMMARY

The disclosure provides a method of producing extracellular proteins from genus *Tepidimonas*, including fermenting a *Tepidimonas* with a culture medium in an air feeding type to obtain a suspension; wherein the culture medium has a carbon source which is an organic acid selected from a group consisting of acetate, lactate and butyrate; a nitrogen source selected from a group consisting of ammonium sulfate (($NH_4$)$_2SO_4$), ammonium nitrate ($NH_4NO_3$), ammonium chloride ($NH_4Cl$) and urea; a phosphate; a carbonate; magnesium chloride ($MgCl_2$); a yeast extract; and trace elements; and collecting the suspension, wherein the suspension includes the extracellular proteins from genus *Tepidimonas*; and wherein the air feeding condition is about 0-0.1 vvm air feeding rate.

A detailed description is given in the following embodiments with reference to the accompanying drawings.

BRIEF DESCRIPTION OF DRAWINGS

The disclosure can be more fully understood by reading the subsequent detailed description and examples with references made to the accompanying drawings, wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are shown schematically in order to simplify the drawings.

In one embodiment of the present disclosure, a method of producing extracellular proteins from genus *Tepidimonas* is provided. The extracellular proteins can effectively be obtained from the genus *Tepidimonas fonticaldi* by using the methods of the present embodiments.

A method of producing extracellular proteins from genus *Tepidimonas* may include the following steps, but it is not limited thereto.

First, fermenting a *Tepidimonas* with a culture medium in an air feeding type to obtain a suspension. In one embodiment, the bacterium of genus *Tepidimonas* is cultured for about 48-270 hrs.

Examples of the bacterium of genus *Tepidimonas* mentioned above may comprise, but are not limited to *Tepidimonas fonticaldi*, *Tepidimonas ignava*, *Tepidimonas aquatic*, *Tepidimonas taiwanesis*, etc.

In one embodiment, a bacterium of genus *Tepidimonas* of the present disclosure is *Tepidimonas fonticaldi*. The *Tepidimonas fonticaldi* is *Tepidimonas fonticaldi* sp. *nov*., which was deposited at the Laboratorium voor. Microbiologie Gent' Belgium (LMG) on Nov. 21, 2011, and the deposit number is LMG26746.

In another one embodiment, a bacterium of genus *Tepidimonas* of the present disclosure is *Tepidimonas fonticaldi*. The *Tepidimonas fonticaldi* is *Tepidimonas fonticaldi* sp. *nov*., which was deposited at the Korean Collection for Type Cultures (KCTC) on Dec. 4, 2013, and the deposit number is KCTC 12528BP. The *Tepidimonas fonticaldi* sp. *nov*. KCTC 12528BP is capable of producing extracellular proteins.

The culturing medium for culturing a bacterium of genus *Tepidimonas* of the present disclosure may comprise, but is not limited to, a carbon source, a nitrogen source, phosphate, magnesium chloride ($MgCl_2$), yeast extract and trace elements.

The culturing medium of genus *Tepidimonas* of the present disclosure is not limited to, but may comprise, a carbon source, a nitrogen source, a phosphate, a carbonate, magnesium chloride ($MgCl_2$), a yeast extract and trace elements.

In some embodiments, the above-mentioned carbon source for the culturing medium is an organic acid, and examples of the above-mentioned organic acid may comprise, but are not limited to, acetate, lactate, butyrate, etc. In one embodiment, the above-mentioned carbon source may be acetate.

Moreover, in some embodiments, the above-mentioned nitrogen source for the culturing medium may comprise ammonium sulfate (($NH_4)_2SO_4$), ammonium nitrate ($NH_4NO_3$), ammonium chloride ($NH_4Cl$), urea, etc., but it is not limited thereto. In one embodiment, the above-mentioned nitrogen source may be ammonium sulfate (($NH_4)_2SO_4$).

In some embodiments, the suitable phosphate for the culturing medium may comprise, but is not limited to, disodium hydrogen phosphate ($Na_2HPO_4$), potassium dihydrogen phosphate ($KH_2PO_4$), sodium dihydrogen phosphate ($NaH_2PO_4$), dipotassium phosphate ($K_2HPO_4$), etc. or any combination thereof.

In some embodiments, the carbonate for the culturing medium may comprise, but is not limited to, sodium bicarbonate ($NaHCO_3$).

Furthermore, the trace elements for the culturing medium may comprise, for example, zinc (Zn), manganese (Mn), boron (B), cobalt (Co), copper (Cu), nickel (Ni), molybdenum (Mo), etc, but is not limited thereto. In one embodiment, the trace elements in the culturing medium of the present disclosure may comprise zinc, manganese, boron, cobalt, copper, nickel and molybdenum. In this embodiment, the respective element may be in the forms shown in the following, but is not limited thereto: zinc may be in the form of zinc sulfate ($ZnSO_4$), manganese may be in the form of manganese chloride ($MnCl_2$), boron may be in the form of boric acid ($H_3BO_3$), cobalt may be in the form of cobalt chloride ($CoCl_2$), copper may be in the form of copper chloride ($CuCl_2$), Ni may be in the form of nickel chloride ($NiCl_2$), and Mo is sodium molybdate ($Na_2MoO_4$).

In the culturing medium of one embodiment, the content of the carbon source may be about 0.1 g/L-15 g/L, the content of the nitrogen source may be about 0.1 g/L-15 g/L, the content of the phosphate may be about 0.1 g/L-30 g/L, the content of the carbonate may be about 0.1 g/L-20 g/L, the content of the $MgCl_2$ may be about 0.01 g/L-10 g/L, the content of the yeast extract may be about 0.1 g/L-20 g/L, and the content of the trace elements may be about 0.01 g/L-1 g/L, but it is not limited thereto.

In the culturing medium of one embodiment, the carbon-nitrogen weight ratio of the carbon source to the nitrogen source may be about 1-60, and in another embodiment, the carbon-nitrogen weight ratio of the carbon source to the nitrogen source may be about 11.

In one embodiment, the fermenting step is conducted in a fermenter, but it is not limited thereto. In an exemplary embodiment, liquid capacity of the fermenter is 5 L. In another embodiment, liquid capacity of the fermenter is 100 L. In another embodiment, liquid capacity of the fermenter may be is ton-level.

The fermenting step comprises a stirring step, in which the stirring rate may be about 50-500 rpm, and in another embodiment, the stirring rate may be about 200 rpm, but it is not limited thereto.

In the fermenting step the bacterium of genus *Tepidimonas* is cultured at about 40-80° C. In one embodiment, the bacterium of genus *Tepidimonas* is cultured at about 50° C.

The fermenting step conducted in a fermenter may comprise feeding air into the culture medium, or it may not be necessary. When air feeding, the air feeding rate for the fermenting is about 0-0.1 vvm, but it is not limited thereto. Furthermore, when the air feeding rate is 0 vvm, it means the fermenting step is performed without air feeding. In one embodiment, the gas used for the air feeding may comprise, but is not limited to, air.

Figure 1A:
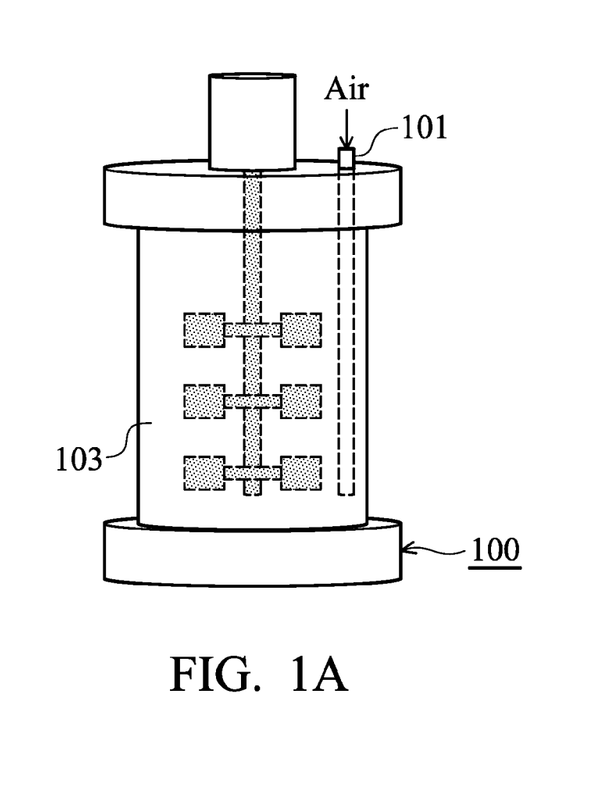
FIG. 1A shows an air feeding type directly feeding the air into the bottom of the culture medium according to an embodiment of the disclosure.
Figure 1B:
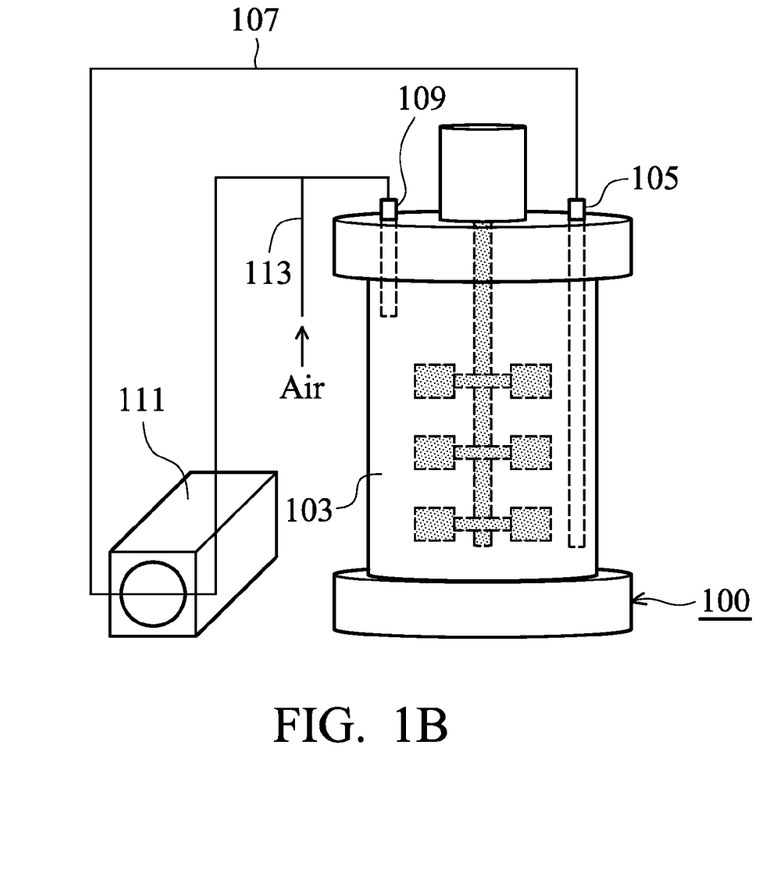
FIG. 1B shows an air feeding type according to another embodiment of the disclosure, circulating the culture medium by introducing the medium out from the fermenter and sending it back into the fermenter and, during the circulation, the air is mixed into the culture medium before it is sent back.
Figure 1C:
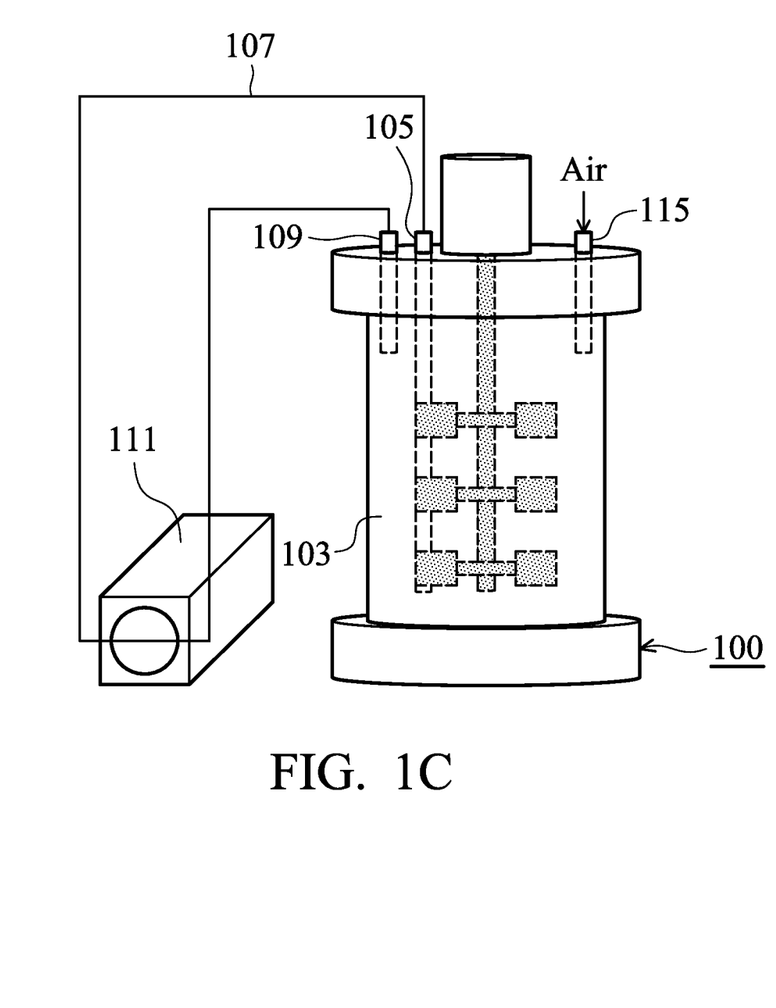
FIG. 1C shows an air feeding type according to another embodiment of the disclosure, circulating the culture medium by introducing the medium out from the fermenter and sending it back into the fermenter and feeding the air into the top of the fermenter.

In one embodiment, the fermenting is conducted in a fermenter, and the air feeding condition may comprise three feeding types, shown in FIGS. 1A, 1B and 1C, but it is not limited thereto.

In the first air feeding type, air is fed directly into the bottom of the culture medium. As shown in FIG. 1A, the air is fed into the bottom of the culture medium 103 via piping 101 extending from the top of the fermenter 100.

The second air feeding type involves circulating the culture medium by introducing the medium out from the fermenter and sending it back into the fermenter and, during the circulation, the air is mixed into the culture medium before it is sent back. FIG. 1B shows how the culturing medium 103 is introduced from the fermenter 100 via an internal piping 105 and sent back to the fermenter 100 via an external piping 107 to form an outer liquid circulation 111, and air is mixed into the culturing medium 103 before it is sent back via piping 113.

The third air feeding type is circulating the culture medium by introducing the medium out from the fermenter and sending it back into the fermenter and feeding the air into the top of the fermenter. FIG. 1C shows how the culturing medium is introduced out from the fermenter via the internal piping 105 and culturing medium via the external piping 107 to form an outer liquid circulation 111 that is sent back to the fermenter via another external piping 109, and the air is fed into the top of the culture medium 103 via piping 115.

In one embodiment, the air feeding type involves directly feeding a gas into the bottom of the culture medium, and the gas is air. In one example, the air feeding rate for the fermenting is about 0.001-0.1 vvm, or it may be about 0.025 vvm.

In one embodiment, the air feeding type involves circulating the culture medium by introducing the medium out from the fermenter and sending it back into the fermenter and, during the circulation, a gas is mixed into the culture medium before it is sent back, in one embodiment in which the gas is air, and the air feeding rate for the fermenting is about 0.001-0.1 vvm, or it may be about 0.025 vvm, and the medium circulation ratio is about 0.1-12 L/hr, or it may be about 3 L/hr.

Moreover, in the method for producing extracellular protein from genus *Tepidimonas* of the present disclosure, the initial pH of the culture medium is pH 5-pH 9, but it is not limited thereto. In one embodiment, the initial pH of the culture medium is about pH 7.

In the foregoing method for producing extracellular protein from genus *Tepidimonas* of the present disclosure, in fermenting, the final pH of the culture medium is about pH 4-pH 10, but it is not limited thereto. In one embodiment, the final pH of the culture medium is about pH 8.

Furthermore, in the method for producing extracellular protein from genus *Tepidimonas* of the present disclosure, the concentration of *Tepidimonas* for culturing is 0.1-40 V % of the medium, for example, 5 V %, but it is not limited thereto.

In one embodiment, the culturing medium for the method of producing extracellular proteins from genus *Tepidimonas*, including a carbon source, a nitrogen source, a phosphate, a carbonate, a magnesium chloride ($MgCl_2$), a yeast extract and trace elements, the carbon source which is acetate, the nitrogen source which is ammonium sulfate ($(NH4)_2SO_4$), the carbonate which is sodium bicarbonate ($NaHCO_3$), the content of the acetate may be about 0.1 g/L-15 g/L, the content of the ammonium sulfate may be about 0.1 g/L-15 g/L, the content of the phosphate may be about 0.1 g/L-30 g/L, the content of the sodium bicarbonate may be about 0.1 g/L-20 g/L, the content of the $MgCl_2$ may be about 0.01 g/L-10 g/L, the content of the yeast extract may be about 0.2 g/L-5 g/L, and the content of the trace elements may be about 0.01 g/L-1 g/L.

In the foregoing method for producing extracellular protein from genus *Tepidimonas* of the present disclosure, wherein the fermenting is conducted in a fermenter, wherein the concentration of *Tepidimonas* for culturing is 0.1-40 V % of the medium, the initial pH of the culture medium is pH 5-pH 9, the final pH of the culture medium is about pH 4-pH 10, the stirring rate for the fermenting is about 50-500 rpm, the temperature for the fermentation is about 40-80° C., the air feeding type is circulating the culture medium by introducing the medium out from the fermenter and sending it back into the fermenter and, during the circulation, a gas is mixed into the culture medium before it is sent back, the circulation ratio is about 0.1-12 L/hr, the gas is air, and the air feeding rate for the fermenting is about 0.001-0.1 vvm.

Furthermore, in the embodiment mentioned above, culturing a *Tepidimonas* into a culturing medium for fermentation to obtain a suspension, the suspension comprises extracellular proteins from genus *Tepidimonas*.

The extracellular proteins can effectively be obtained from the genus *Tepidimonas* by using the methods of the present embodiments.

EXAMPLES

Example 1

Temperature effect on producing extracellular protein of genus *Tepidimonas* KCTC 12528BP The *Tepidimonas* KCTC 12528BP was cultured at different respective temperatures to determine the most suitable culturing temperatures for a 5 L fermenter. The testing temperatures were 45° C., 50° C., and 55° C.

The *Tepidimonas* KCTC 12528BP was cultured by a medium shown in the following Table 1. In the culturing medium, the concentration of acetate was 3.11 g/L, ammonium sulfate was 0.53 g/L, and the carbon-nitrogen weight ratio was 11. The culturing condition was the initial bacterial cell concentration of about $OD_{600}$ 0.03, an initial pH value of 7.0, a stirring rate of 200 rpm, total volume of reaction was 4 L, and the culturing time was 80 hours.

TABLE 1

| Ingredients for the culturing medium | |
| --- | --- |
| Ingredients | Content (g/L) |
| Acetate | 3.11 |
| $NaHCO_3$ | 2.49 |
| $KH_2PO_4$ | 1.50 |
| $(NH_4)_2SO_4$ | 0.53 |
| Yeast extract | 1.00 |
| $MgCl_2$ | 0.10 |
| Trace element solution (Ingredients shown below) | 1 mL/L |
| Trace element solution | |
| $ZnSO_4 \cdot 7H_2O$ | 0.10 |
| $MnCl_2 \cdot 4H_2O$ | 0.03 |
| $H_3BO_3$ | 0.30 |
| $CoCl_2 \cdot 6H_2O$ | 0.20 |
| $CuCl_2 \cdot 2H_2O$ | 0.01 |
| $NiCl_2 \cdot 6H_2O$ | 0.02 |
| $Na_2MoO_4 \cdot 2H_2O$ | 0.03 |

Figure 2:
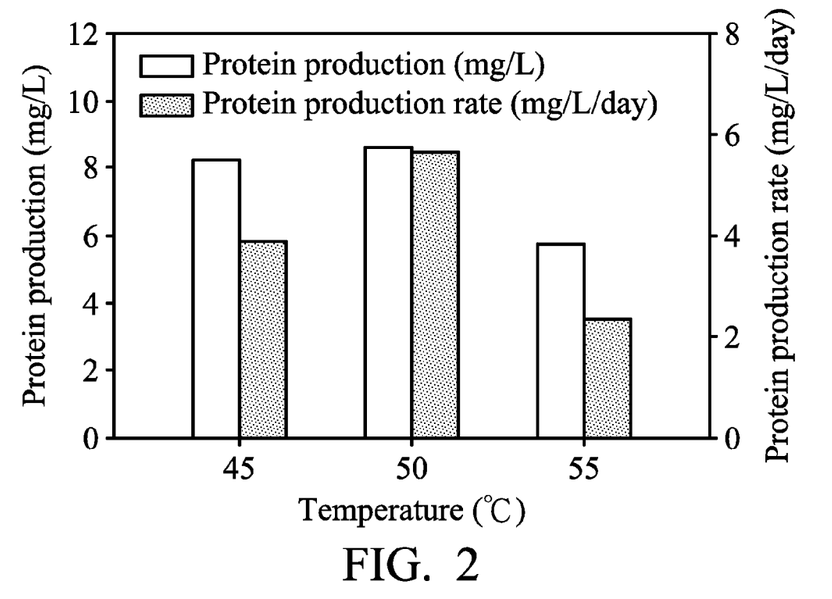
FIG. 2 shows the protein yields and production rates of culturing *Tepidimonas fonticaldi* sp. nov. KCTC 12528BP at different culturing temperatures according to one embodiment of the disclosure.

FIG. 2 shows the protein yields and production rates of culturing *Tepidimonas fonticaldi* sp. *nov*. KCTC 12528BP at different culturing temperatures.

According to FIG. 2, the protein concentration and the protein yields at 50° C. were better than those at 45° C. and 55° C., respectively is 8.59 mg/L and 5.67 mg/L per day at 50° C.

Therefore, 50° C. was the optimum culturing temperature for producing extracellular proteins from *Tepidimonas fonticaldi* sp. *nov*. KCTC 12528BP.

Example 2

Air feeding rate effect on producing extracellular protein of genus *Tepidimonas* KCTC 12528BP Bacteria of *Tepidimonas fonticaldi* sp. *nov*. KCTC 12528BP are slightly thermophilic bacteria. The *Tepidimonas* KCTC 12528BP was cultured at different air feeding rates to determine a suitable air feeding rate for a 5 L fermenter. The testing air feeding rates were 0 vvm, 0.0125 vvm, and 0.025 vvm. The air feeding type was directly feeding the air into the bottom of the culture medium, as shown in FIG. 1A.

The *Tepidimonas* KCTC 12528BP was cultured by the culture medium with the ingredients shown in Table 1. In the culturing medium, the concentration of acetate was 3.11 g/L, ammonium sulfate was 0.53 g/L, and the carbon-nitrogen weight ratio was 11. The culturing condition was the initial bacterial cell concentration of about $OD_{600}$ 0.03, an initial pH value of 7.0, a stirring rate of 200 rpm, total volume of reaction was 4 L, and the culturing time was 80 hours.

Figure 3:
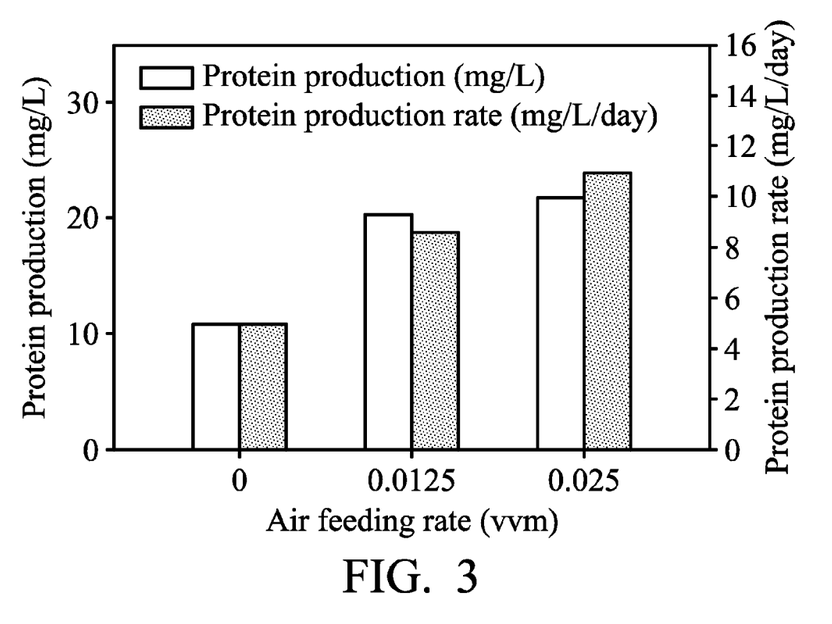
FIG. 3 shows the protein yields and production rates of culturing *Tepidimonas fonticaldi* sp. nov. KCTC 12528BP at different air feeding rate according to one embodiment of the disclosure.

FIG. 3 shows the protein yields and production rates of culturing *Tepidimonas fonticaldi* sp. *nov*. KCTC 12528BP at different air feeding rates.

According to FIG. 3, the protein concentration and the protein yields at 0.025 vvm were higher than 0 vvm and 0.0125 vvm, respectively, at 21.77 mg/L and 10.90 mg/L per day.

Therefore, in the later examples, the air feeding rate was controlled at 0.025 vvm for feeding. The suitable final pH value and liquid circulation rate for increasing protein concentration and protein production were also investigated.

Example 3

Air feeding type effect on producing extracellular protein of genus *Tepidimonas* KCTC 12528BP According to Example 2, it is known that directly feeding the air into the bottom of the culture medium caused a gas-lift phenomenon at the culture system. When gas-lift increased, it resulted the protein concentration and protein concentration decreased. The *Tepidimonas* KCTC 12528BP was cultured with different air feeding types to determine the most suitable air feeding type for a 5 L fermenter. The testing types were (a) directly feeding the air into the bottom of the culture medium (referred to FIG. 1A), (b) circulating the culture medium by introducing the medium out from the fermenter and sending it back into the fermenter and, during the circulation, the air is mixed into the culture medium before it is sent back (referred to FIG. 1B), and (c) circulating the culture medium by introducing the medium out from the fermenter and sending it back into the fermenter and feeding the air into the top of the fermenter (referred to FIG. 1C).

The *Tepidimonas fonticaldi* sp. *nov*. KCTC 12528BP was cultured with the culture medium ingredients shown in Table 1. In the culturing medium, the concentration of acetate was 3.11 g/L, ammonium sulfate was 0.53 g/L, and the carbon-nitrogen weight ratio was 11. The culturing condition was the initial bacterial cell concentration of about $OD_{600}$ 0.03, an initial pH value of 7.0, a stirring rate of 200 rpm, a culturing temperature of 50° C., a feeding rate of 0.025 vvm, total volume of reaction was 4 L, and the culturing time was 130 hours.

Figure 4:
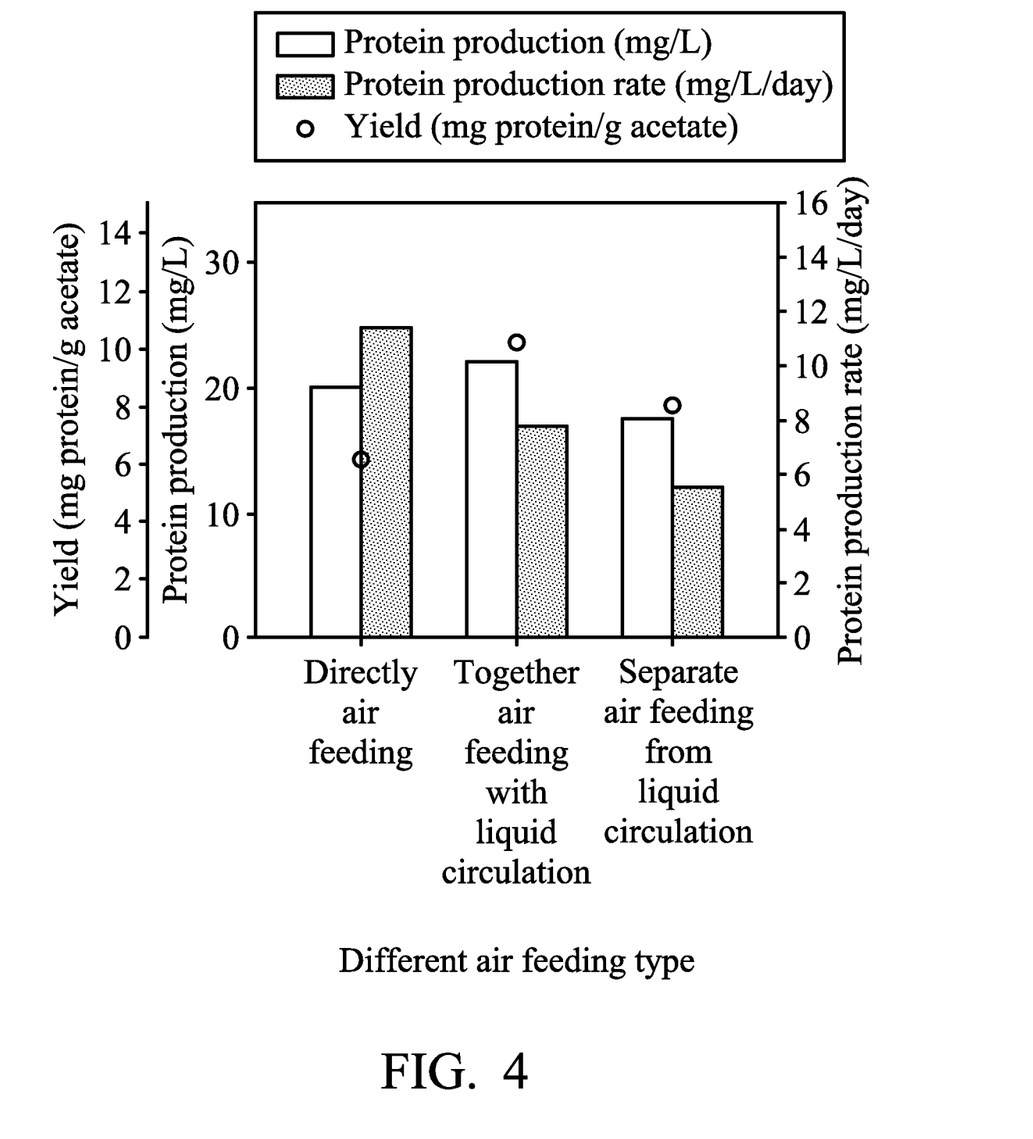
FIG. 4 show the protein yields, production rates and per gram of acetate of protein yields of culturing *Tepidimonas fonticaldi* sp. nov. KCTC 12528BP at different air feeding types according to one embodiment of the disclosure.

According to FIG. 4, it shows that the protein yields, production rates and protein yields of per gram of acetate at different air feeding types.

The protein production rate rises to about 11.45 mg/L/day using the direct air feeding type (type a), which is the best of the three types. However, the direct air feeding type (type a) caused the gas-lift phenomenon and decreased the protein yields of per gram of acetate.

In other words, air feeding type (b) (circulating the culture medium by introducing the medium out from the fermenter and sending it back into the fermenter and, during the circulation, the air is mixed into the culture medium before it is sent back) has a higher concentration of protein production and protein yields of per gram of acetate than type (a) and type (c). However, using the air feeding type (b) to culture *Tepidimonas fonticaldi* sp. *nov*. KCTC 12528BP, the protein production rate is slightly lower than using the air feeding type (a), presuming the effect was medium liquid circulation rates.

The protein concentration and protein production rates in the air feeding type (c) are lower than the air feeding type (a) and (b) for culturing *Tepidimonas fonticaldi* sp. *nov*. KCTC 12528BP.

According to measure result it is knows that concentration of protein and per gram of acetate of protein yields. In the later examples the air feeding type was (b), effect of the final pH value and rate of liquid circulation was investigated, for increased to protein concentration and protein production.

Example 4

Final pH value effect on producing extracellular protein of *Tepidimonas fonticaldi* sp. *nov*. KCTC 12528BP The pH value of the culturing medium will directly affect the bacterial growth, thereby affecting the protein concentration. From the previous experiments, it is known that the pH value of culture anaphase is higher than pH 8.5. The *Tepidimonas* KCTC 12528BP was cultured at different respective final pH values to determine a suitable final pH value for a 5 L fermenter. The testing final pH value of pH 7.5, pH 8, or pH 8.5.

The *Tepidimonas fonticaldi* sp. *nov*. KCTC 12528BP was cultured with the culture medium ingredients shown in Table 1. In the culturing medium, the concentration of acetate was 3.11 g/L, ammonium sulfate was 0.53 g/L, and the carbon-nitrogen weight ratio was 11. The culturing condition was the initial bacterial cell concentration of about $OD_{600}$ 0.03, an initial pH value of 7.0, a stirring rate of 200 rpm, a culturing temperature of 50° C., a feeding rate of 0.025 vvm, a liquid circulation rate of 1.5 L/hr (the air feeding type (a) or (b)), the total volume of reaction was 4 L, and the culturing time was 250 hours.

Figure 5:
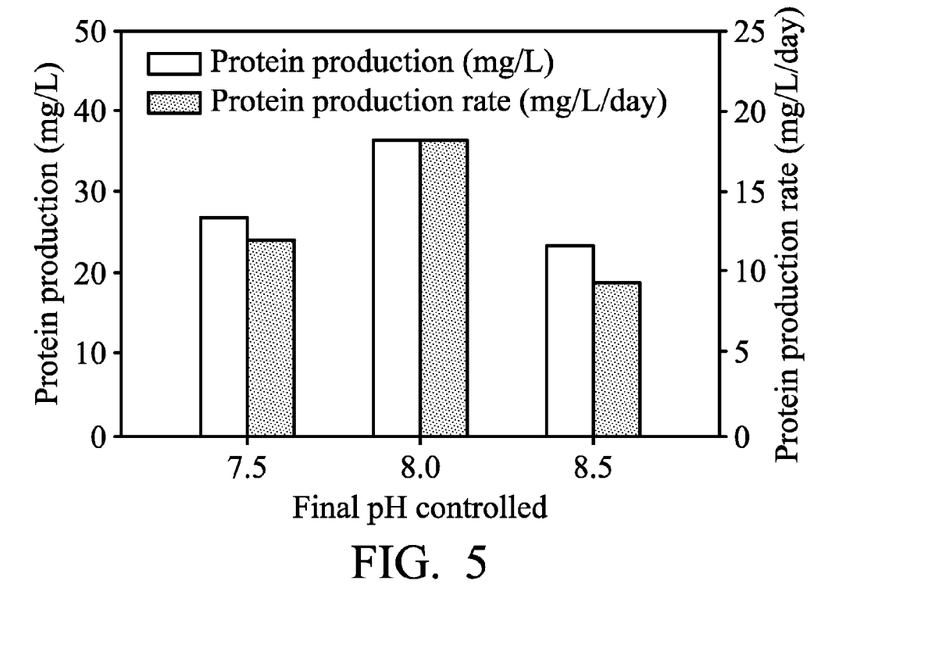
FIG. 5 shows the protein yields and production rates of culturing *Tepidimonas fonticaldi* sp. nov. KCTC 12528BP at different final pH of the fermenting according to one embodiment of the disclosure.

The results are shown in FIG. 5. It shows the protein concentration and protein production rate of culturing *Tepidimonas fonticaldi* sp. *nov*. KCTC 12528BP at different final pH values.

According to FIG. 5, the bacterial and protein concentration was improved. Thus, controlling the final pH value was an essential factor and it would directly affect protein production. When the final pH value was controlled at 8.0, the protein production concentration and protein production rate are about 36.84 mg/L and 18.17 mg/L/day, respectively, and better than pH 7.5 and pH 8.5.

Thus, in the later experiments, controlling the final pH value of the culturing medium at pH 8.0.

Example 5

Rate of liquid circulation effect on secreting extracellular protein of *Tepidimonas fonticaldi* sp. *nov*. KCTC 12528BP In one embodiment, culturing *Tepidimonas fonticaldi* sp. *nov*. KCTC 12528BP was performed in a 5 L fermenter at different liquid circulation rates for circulating the culture medium by introducing the medium out from the fermenter and sending it back into the fermenter and, during the circulation, the air is mixed into the culture medium before it is sent back, to determine a suitable rate of liquid circulation. The testing bacterial was cultured under liquid circulation rates of 1.5 L/hr, 3.0 L/hr or 6.0 L/hr.

The *Tepidimonas fonticaldi* sp. *nov*. KCTC 12528BP was cultured using the culture medium ingredients shown in Table 1. In the culturing medium, the concentration of acetate was 3.11 g/L, ammonium sulfate was 0.53 g/L, and the carbon-nitrogen weight ratio was 11. The culturing condition was the initial bacterial cell concentration of about $OD_{600}$ 0.03, an initial pH value of 7.0, a final pH values of 8.0, a stirring rate of 200 rpm, a culturing temperature of 50° C., a feeding rate of 0.025 vvm, the total volume of the reaction was 4 L, and the culturing time was 240 hours.

Figure 6:
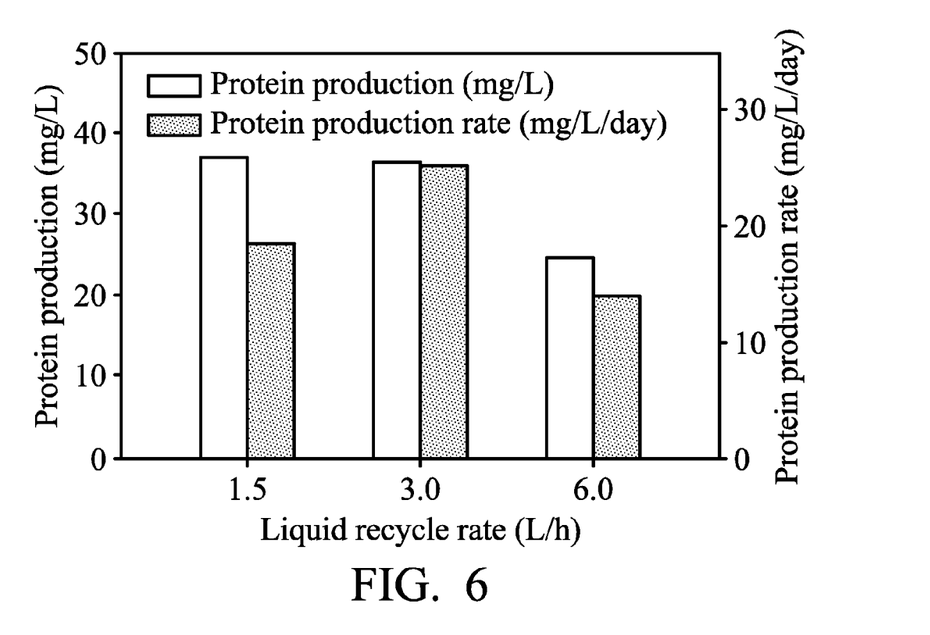
FIG. 6 shows culturing *Tepidimonas fonticaldi* sp. nov. KCTC 12528BP circulating the culture medium by introducing the medium out from the fermenter and sending it back into the fermenter and, during the circulation, the air is mixed into the culture medium before it is sent back at different circulation rates of the protein yields and production rates of culturing *Tepidimonas fonticaldi* sp. nov. KCTC 12528BP according to one embodiment of the disclosure.

FIG. 6 shows the protein concentration and protein production rate of culturing *Tepidimonas fonticaldi* sp. *nov*. KCTC 12528BP at different liquid circulation rates. The air feeding type involves circulating the culture medium by introducing the medium out from the fermenter and sending it back into the fermenter and, during the circulation, a gas is mixed into the culture medium before it is sent back.

According to FIG. 6, the liquid circulation rates of 1.5 L/hr and 3.0 L/hr could effectively improve protein production concentration and protein production rates, except liquid circulation rates of 6.0 L/hr. Furthermore, when the liquid circulation rate was controlled at 3.0 L/hr, the protein production concentration and protein production rate was higher than under a liquid circulation rate of 1.5 L/hr. The protein concentration and protein production rate were about 36.43 mg/L and 25.14 mg/L.

Thus, the liquid circulation rate of 3.0 L/hr in a 5 L fermenter could be considered for use in a 100 L fermenter.

Example 6

Different amounts of bacterial strain implanted into culture medium effect on secreting extracellular protein of *Tepidimonas fonticaldi* sp. *nov*. KCTC 12528BP In one embodiment, in culturing the different amounts of *Tepidimonas fonticaldi* sp. *nov*. KCTC 12528BP in a 100 L fermenter. The testing amount of inoculation were 2.5 V %, 5.0 V %, or 10.0 V %. (inoculation concentration of *Tepidimonas fonticaldi* sp. *nov*. KCTC 12528BP is about $OD_{600}$=1.5).

The *Tepidimonas fonticaldi* sp. *nov*. KCTC 12528BP was cultured using the culture medium ingredients shown in Table 1. In the culturing medium, the concentration of acetate was 3.11 g/L, ammonium sulfate was 0.53 g/L, and the carbon-nitrogen weight ratio was 11. The culturing condition was the initial bacterial cell concentration of about $OD_{600}$ 0.03, an initial pH value of 7.0, a final pH value of 8.0, a stirring rate of 200 rpm, a culturing temperature of 50° C., the liquid circulation rates of 3.0 L/hr (circulating the culture medium by introducing the medium out from the fermenter and sending it back into the fermenter and, during the circulation, the air is mixed into the culture medium before it is sent back), total volume of reaction was 80 L, and the culturing time was 225 hours.

Figure 7:
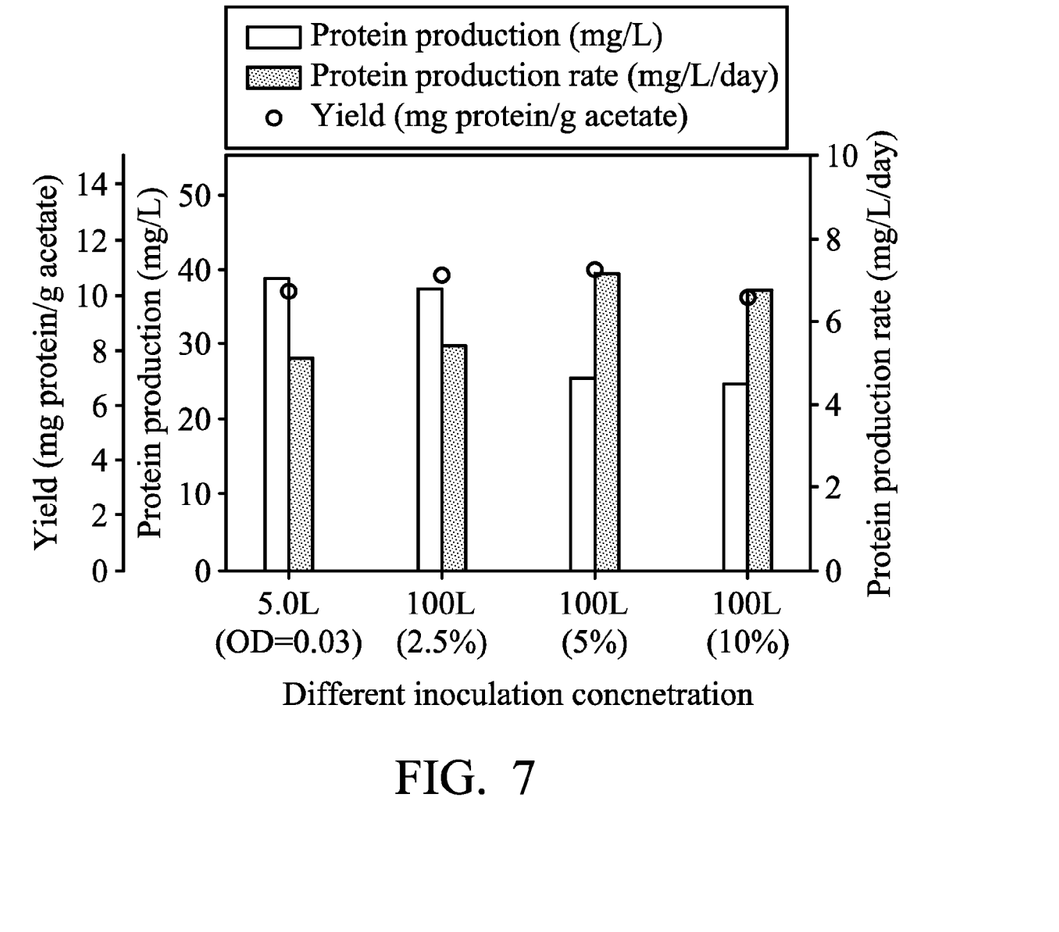
FIG. 7 shows the protein yields and production rates of culturing *Tepidimonas fonticaldi* sp. nov. KCTC 12528BP at different inoculation concentrations according to one embodiment of the disclosure.

The results are shown as FIG. 7. It shows under different amounts of inoculation into the culture medium, the concentration of the protein and protein production rate of *Tepidimonas fonticaldi* sp. *nov*. KCTC 12528BP.

According to FIG. 7, it is known that when the bacterial strain was inoculation into the culture medium of 5 v %, the maximum mean of protein production rate of *Tepidimonas fonticaldi* sp. *nov*. KCTC 12528BP is the largest, and the production of protein yields are constant.

Therefore, the 5 v % implant amount could be used in a 100 L fermenter for protein production.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A method of producing extracellular proteins from genus *Tepidimonas*, comprising:
    fermenting a *Tepidimonas* in a fermenter with a culture medium in an air feeding type to obtain a suspension; and
    wherein the culture medium comprises:
    a carbon source which is an organic acid, selected from a group consisting of acetate, lactate and butyrate;
    a nitrogen source selected from a group consisting of ammonium sulfate (($NH_4$)$_2$$SO_4$), ammonium nitrate ($NH_4NO_3$), ammonium chloride ($NH_4Cl$) and urea;
    a phosphate;
    a carbonate;
    magnesium chloride ($MgCl_2$);
    a yeast extract; and
    trace elements;
    collecting the suspension, the suspension comprising the extracellular proteins from genus *Tepidimonas*,
    wherein the air feeding type is about 0.001-0.1 vvm air feeding rate.

2. The method of producing extracellular proteins from genus *Tepidimonas* as claimed in claim 1, wherein the genus *Tepidimonas* comprises *Tepidimonas fonticaldi*, *Tepidimonas ignava*, *Tepidimonas aquatic* or *Tepidimonas taiwanesis*.

3. The method of producing extracellular proteins from genus *Tepidimonas* as claimed in claim 1, wherein the *Tepidimonas* is *Tepidimonas fonticaldi* sp. *nov*.

4. The method of producing extracellular proteins from genus *Tepidimonas* as claimed in claim 3, wherein the *Tepidimonas fonticaldi* is *Tepidimonas fonticaldi* sp. *nov* KCTC 12528BP.

5. The method of producing extracellular proteins from genus *Tepidimonas* as claimed in claim 1, wherein the content of the carbon source is about 0.1 g/L-15 g/L, the content of the nitrogen source is about 0.1 g/L-15 g/L, the content of the phosphate is about 0.1 g/L-30 g/L, the content of the carbonate is about 0.1 g/L-20 g/L, the content of the $MgCl_2$ is about 0.01 g/L-10 g/L, the content of the yeast extract is about 0.1 g/L-20 g/L, and the content of the trace elements is about 0.01 g/L-1 g/L.

6. The method of producing extracellular proteins from genus *Tepidimonas* as claimed in claim 1, wherein the carbon-nitrogen weight ratio of the carbon source to the nitrogen source is about 1-20 in the culture medium.

7. The method of producing extracellular proteins from genus *Tepidimonas* as claimed in claim 1, wherein the carbon source is acetate.

8. The method of producing extracellular proteins from genus *Tepidimonas* as claimed in claim 1, wherein the nitrogen source is ammonium sulfate (($NH_4$)$_2$$SO_4$).

9. The method of producing extracellular proteins from genus *Tepidimonas* as claimed in claim 1, wherein the phosphate comprises potassium dihydrogen phosphate ($KH_2PO4$), disodium hydrogen phosphate ($Na_2HPO_4$) or dipotassium phosphate ($K_2HPO_4$).

10. The method of producing extracellular proteins from genus *Tepidimonas* as claimed in claim 1, wherein the phosphate is dipotassium phosphate ($K_2HPO_4$).

11. The method of producing extracellular proteins from genus *Tepidimonas* as claimed in claim 1, wherein the carbonate is sodium bicarbonate ($NaHCO_3$).

12. The method of producing extracellular proteins from genus *Tepidimonas* as claimed in claim 1, wherein the trace elements comprises zinc (Zn), manganese (Mn), boron (B), cobalt (Co), copper (Cu), nickel (Ni) and molybdenum (Mo).

13. The method of producing extracellular proteins from genus *Tepidimonas* as claimed in claim 1, wherein the fermenting step is in a stirring which the stirring rate is about 50-500 rpm.

14. The method of producing extracellular proteins from genus *Tepidimonas* as claimed in claim 1, wherein the fermenting step is stirring at the rate of about 200 rpm.

15. The method of producing extracellular proteins from genus *Tepidimonas* as claimed in claim 1, wherein the temperature of fermenting step is about 40-80° C.

16. The method of producing extracellular proteins from genus *Tepidimonas* as claimed in claim 1, wherein the temperature of fermenting step is about 50° C.

17. The method of producing extracellular proteins from genus *Tepidimonas* as claimed in claim 1, wherein the air feeding of fermenting step is comprises an air.

18. The method of producing extracellular proteins from genus *Tepidimonas* as claimed in claim 1, wherein the fermenting is conducted in a fermenter, the air feeding type comprises directly feeding the air into the bottom of the culture medium; circulating the culture medium by introducing the medium out from the fermenter and sending it back into the fermenter and, during the circulation, the air is mixed into the culture medium before it is sent back; or circulating the culture medium by introducing the medium out from the fermenter and sending it back into the fermenter and feeding the air into the top of the fermenter.

19. The method of producing extracellular proteins from genus *Tepidimonas* as claimed in claim 1, wherein the fermenting is conducted in a fermenter, and the air feeding type is directly feeding the air into the bottom of the culture medium.

20. The method of producing extracellular proteins from genus *Tepidimonas* as claimed in claim 19, wherein an air feeding for the fermenting is air.

21. The method of producing extracellular proteins from genus *Tepidimonas* as claimed in claim 20, wherein the air feeding rate for the fermenting is about 0.001-0.1 vvm.

22. The method of producing extracellular proteins from genus *Tepidimonas* as claimed in claim 20, wherein the air feeding rate for the fermenting is about 0.025 vvm.

23. The method of producing extracellular proteins from genus *Tepidimonas* as claimed in claim 1, wherein the fermenting is conducted in a fermenter, and circulating the culture medium by introducing the medium out from the fermenter and sending it back into the fermenter in which, during the circulation, the air is mixed into the culture medium before it is sent back.

24. The method of producing extracellular proteins from genus *Tepidimonas* as claimed in claim 23, wherein the air mixing for circulating is feeding air.

25. The method of producing extracellular proteins from genus *Tepidimonas* as claimed in claim 23, wherein the medium circulation rate is about 0.1-12 L/hr.

26. The method of producing extracellular proteins from genus *Tepidimonas* as claimed in claim 23, wherein the medium circulation rate is about 3 L/hr.

27. The method of producing extracellular proteins from genus *Tepidimonas* as claimed in claim 24, wherein the air feeding rate for the feeding is about 0.001-0.1 vvm.

28. The method of producing extracellular proteins from genus *Tepidimonas* as claimed in claim 24, wherein the air feeding rate for the feeding is about 0.025 vvm.

29. The method of producing extracellular proteins from genus *Tepidimonas* as claimed in claim 24, wherein the medium circulation rate is about 3 L/hr, and the air feeding rate for feeding is about 0.025 vvm.

30. The method of producing extracellular proteins from genus *Tepidimonas* as claimed in claim 1, wherein an initial pH of the fermenting is about pH 5-pH 9.

31. The method of producing extracellular proteins from genus *Tepidimonas* as claimed in claim 1, wherein an initial pH of the fermenting is about pH 7.

32. The method of producing extracellular proteins from genus *Tepidimonas* as claimed in claim 1, wherein a final pH of the fermenting is about pH 4-pH 10.

33. The method of producing extracellular proteins from genus *Tepidimonas* as claimed in claim 1, wherein an initial pH of the fermenting is about pH 8.

34. The method of producing extracellular proteins from genus *Tepidimonas* as claimed in claim 1, wherein an initial concentration of *Tepidimonas* for fermenting is 0.1-40 V % of the culture medium.

35. The method of producing extracellular proteins from genus *Tepidimonas* as claimed in claim 1, wherein an initial concentration of *Tepidimonas* for fermenting is 5 V % of the culture medium.

36. The method of producing extracellular proteins from genus *Tepidimonas* as claimed in claim 5, wherein the carbon source is acetate, the nitrogen source is ammonium sulfate (($NH_4$)$_2SO_4$), and the carbonate is sodium bicarbonate ($NaHCO_3$).

37. The method of producing extracellular proteins from genus *Tepidimonas* as claimed in claim 36, wherein the content of the acetate is about 0.1 g/L-15 g/L, the content of the ammonium sulfate is about 0.1 g/L-15 g/L, the content of the phosphate is about 0.1 g/L-30 g/L, the content of the sodium bicarbonate is about 0.1 g/L-20 g/L, the content of the $MgCl_2$ is about 0.01 g/L-10 g/L, the content of the yeast extract is about 0.1 g/L-20 g/L, and the content of the trace elements is about 0.01 g/L-1 g/L.

38. The method of producing extracellular proteins from genus *Tepidimonas* as claimed in claim 37, wherein the fermenting is conducted in the fermenter, wherein an initial concentration of *Tepidimonas* for fermenting is 0.1-40 V % of the medium, an initial pH of the fermenting about pH 5-pH 9, the final pH of the fermenting about pH 4-pH 10, a stirring rate for the fermenting is about 50-500 rpm, a temperature for the fermenting is about 40-80° C., and wherein the fermenting is conducted in a fermenter, circulating the culture medium by introducing the medium out from the fermenter and sending it back into the fermenter in which, during the circulation, the air is mixed into the culture medium before it is sent back, and the air feeding rate about 0.001-0.1 vvm.

\* \* \* \* \*